United States Patent [19]
Burns

[11] Patent Number: 5,131,405
[45] Date of Patent: Jul. 21, 1992

[54] UNIVERSAL BLOOD DRAW SAFETY HOLDER

[75] Inventor: James A. Burns, Elizabeth, N.J.

[73] Assignee: Becton, Dickinson and Company, Franklin Lakes, N.J.

[21] Appl. No.: 584,313

[22] Filed: Sep. 18, 1990

[51] Int. Cl.⁵ .................................... A61B 5/00
[52] U.S. Cl. .................. 128/763; 604/192; 604/263
[58] Field of Search ............ 604/192, 263, 198, 110, 604/411, 412, 414; 128/919, 763-765; 206/365, 366

[56] References Cited

U.S. PATENT DOCUMENTS

| | | | |
|---|---|---|---|
| 4,312,362 | 1/1982 | Kaufman | 128/763 |
| 4,643,199 | 2/1987 | Jennings, Jr. et al. | 128/763 |
| 4,738,663 | 4/1988 | Bogan | 604/198 |
| 4,743,233 | 5/1988 | Schneider | 604/192 |
| 4,747,837 | 5/1988 | Hauck | 604/198 |
| 4,752,290 | 6/1988 | Schramm | 604/198 |
| 4,758,232 | 7/1988 | Chak | 604/220 |
| 4,801,295 | 1/1989 | Spencer | 604/198 |
| 4,826,490 | 5/1989 | Byrne et al. | 604/198 |
| 4,826,491 | 5/1989 | Schramm | 604/198 |
| 4,834,715 | 5/1989 | Hanifli | 604/192 |
| 4,846,808 | 7/1989 | Haber et al. | 604/195 |
| 4,867,172 | 9/1989 | Haber et al. | 128/763 |
| 4,871,355 | 10/1989 | Kikkawa | 604/198 |
| 4,923,446 | 5/1990 | Page et al. | 604/198 |
| 4,927,417 | 5/1990 | Moncada et al. | 604/198 |
| 4,932,940 | 6/1990 | Walker et al. | 604/110 |
| 4,932,945 | 6/1990 | Braginetz et al. | 604/195 |
| 4,938,745 | 7/1990 | Sagstetter | 604/263 |
| 4,947,863 | 8/1990 | Haber et al. | 128/764 |
| 4,991,601 | 2/1991 | Kasai et al. | 128/763 |

Primary Examiner—C. Fred Rosenbaum
Assistant Examiner—Mark O. Polutta
Attorney, Agent, or Firm—Robert P. Grindle

[57] ABSTRACT

A blood draw needle holder is modified on the outside surface of the closed end and the inside surface of the open end so that the closed end of one holder interlocks with the open end of another holder. As a result, one holder with no needle, but identical with another holder with a contaminated needle, may be locked in place over the contaminated needle. In addition, a stationery locking socket is provided for placement on a phlebotomist's tray or cart for locking a new unused holder in place, with the open end of the unused holder facing upright. Thereafter, the phlebotomist inserts the contaminated needle end with its used holder into the unused holder and locks the two together. With such an arrangement, no cumbersome telescoping shield is required on the holder being used for taking a blood sample. A conventional blood draw procedure takes place. The cost is reduced substantially since all holders, whether being used for blood draw or as a shield are identical and made from the same mold. Moreover, a plurality of identical holders may be placed in a single container on the phlebotomist's tray for quickly grabbing one for blood draw use or cover use.

6 Claims, 7 Drawing Sheets

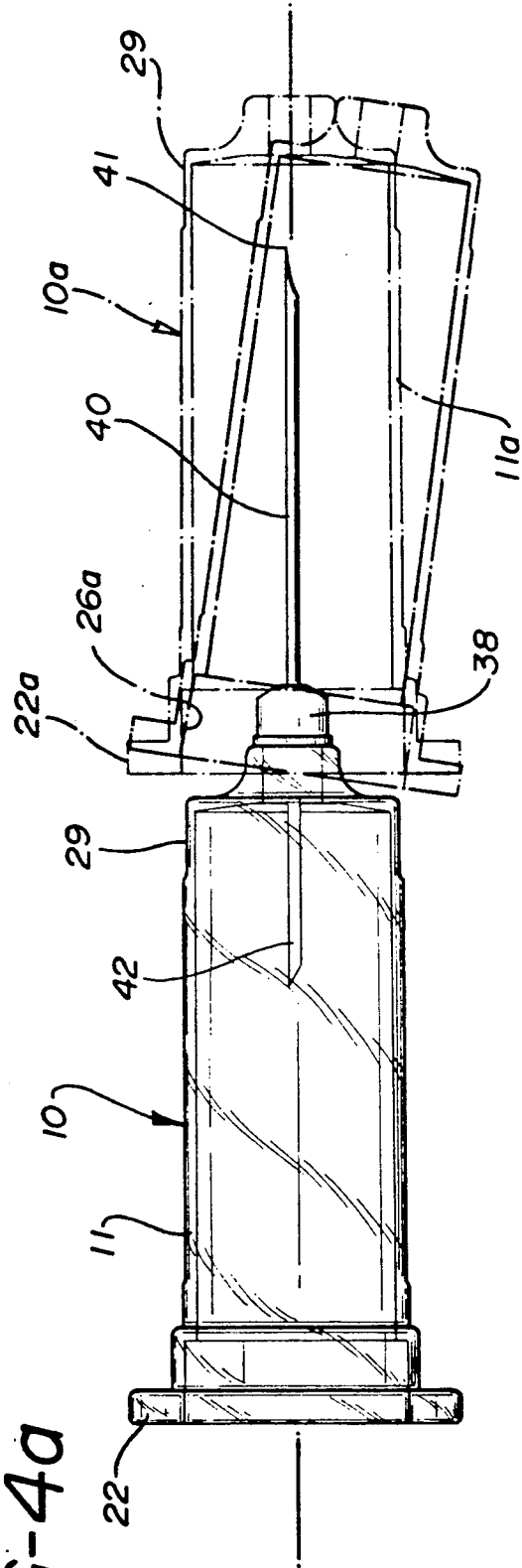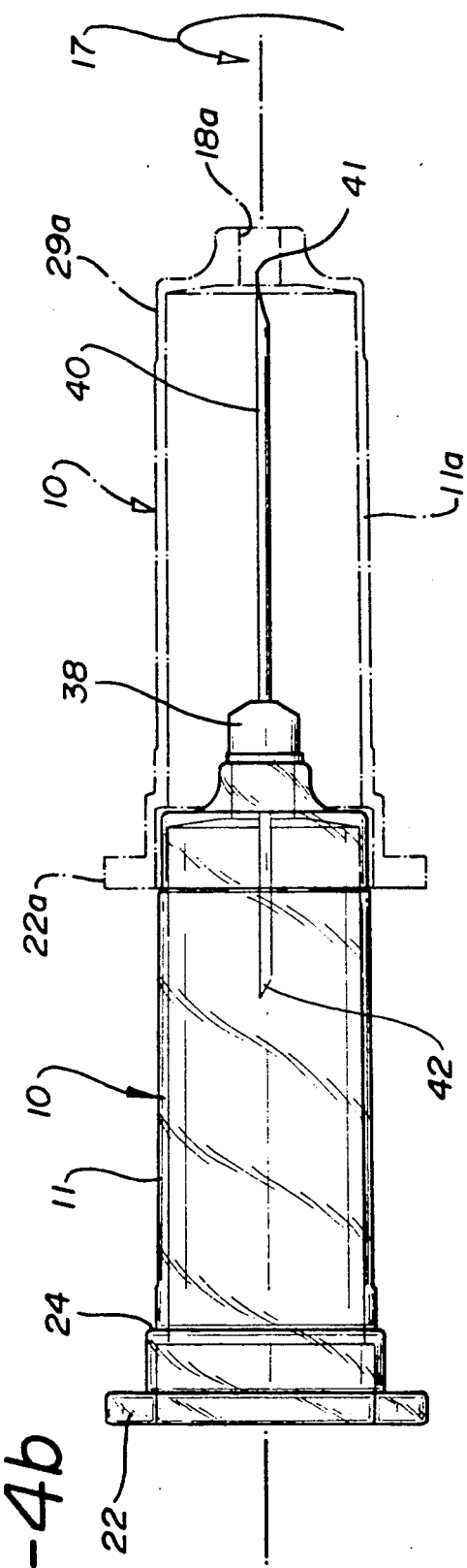

UNIVERSAL BLOOD DRAW SAFETY HOLDER

BACKGROUND AND DESCRIPTION OF THE INVENTION

This invention is directed to yet another arrangement for covering the point of a needle contaminated with body fluid, such as blood, so as to protect the user from accidental needle stick. More particularly, this invention relates to a simplified arrangement for covering the contaminated venous needle end of a double ended needle positioned in a conventional blood draw holder, without the need for some kind of cumbersome separate sliding shield arrangement mounted on the holder, while still providing appropriate protection to the phlebotomist, nurse, doctor or clinical lab technician who may be handling the contaminated needle, once it has been used.

For those familiar with the art to which the present invention is directed, they will understand that there have been a great many inventions developed in the last several years, since the presence of Acquired Immune Deficiency Syndrome (AIDS) has become publicly known, to develop arrangements which will protect the user from being accidentally stuck with a contaminated needle. For example, many inventions have been developed in which a movable shield is mounted coaxially on a blood draw holder during use by the phlebotomist. The separate shield is in a semi-locked position, and the shield is movable to a permanently locked position covering the contaminated needle, once the needle and holder have been used for taking blood samples from a patient. Representative of such art are the following United States patents:

| | |
|---|---|
| 4,752,290 | Issued: June 21, 1988 |
| 4,826,490 | Issued: May 2, 1989 |
| 4,871,355 | Issued: October 3, 1989 |
| 4,826,491 | Issued: May 2, 1989 |
| 4,846,808 | Issued: July 11, 1989 |
| 4,867,172 | Issued: September 19, 1989 |
| 4,938,745 | Issued: July 3, 1990 |

Other arrangements have been developed which are related to the structures described and claimed in the above noted United States patents, but these structures relate to syringes. That is, syringes have barrels in the same manner as blood draw holders, and, therefore, there have been developments wherein a shield is movable from a semilocked position coaxial with a barrel which may be a syringe barrel or it may be a blood draw holder. The shield is moved to a permanent locked position covering a contaminated needle once the device has been used. Of course, syringes are used for injecting medication as well as withdrawing body fluids. At any rate, the needle point is contaminated and the arrangements developed similar to those noted in the above U.S. patents are for, specifically, mounting on a syringe barrel. Representative such devices are described and claimed in the following United States patents.

| | |
|---|---|
| 4,643,199 | Issued: February 17, 1987 |
| 4,743,233 | Issued: May 10, 1988 |
| 4,738,663 | Issued: April 19, 1988 |
| 4,747,837 | Issued: May 31, 1988 |
| 4,801,295 | Issued: January 31, 1989 |
| 4,923,446 | Issued: May 8, 1990 |

| | |
|---|---|
| 4,927,417 | Issued: May 22, 1990 |
| 4,932,940 | Issued: June 12, 1990 |
| 4,932,945 | Issued: June 12, 1990 |

It should be noted that all of the above patents are only representative of the vast amount of prior art available in this field.

With this invention, by contrast, a needle holder arrangement is provided for covering the contaminated negative pressure needle end of blood draw holders, once the needle is removed from the body. The arrangement is such that no cumbersome extra structure is required during the use of the holder of the invention. That is, the holder is modified to have a simple tab like bayonet connection on the outer surface of the closed end portion of the barrel of the needle holder. Moreover, the internal surface of the open end of the holder also has a cooperating tab receiving connection. As a result, one of these modified blood draw holders may be locked end to end with another of the same exact modified holders. As a result of this, one unused holder may cover the contaminated negative pressure needle which has been inserted into a second holder.

With this modification, the phlebotomist or other user of such a holder is not encumbered during the actual sensitive insertion of the needle into the patient for taking a blood sample. This is particularly important for patients who are unusually sensitive to having a needle inserted into their skin. Moreover, it is important to the user for patients whose veins are not easily found for insertion of the needle for taking a blood sample. Also, the angle of needle insertion is not limited by the width of the extra shield mounted on the holder.

Other advantages of the invention here include substantial cost reduction. That is, the holder of the invention requires a single mold for making both the holder which is used and the holder which covers the contaminated needle. Furthermore, the phlebotomist's tray requires only a single container for holders of the type described and claimed in this application. The phlebotomist may select from this single container a holder for use by inserting the conventional two ended needle for taking blood samples. The phlebotomist thereafter, may grab from the same container a holder for covering the contaminated needle, once the blood draw procedure has taken place. This obviates, as will be understood by the practitioner-in-the art, the need for having to modify the blood collection technique which phlebotomists, for example, have developed over a period of years after having taken many many blood samples.

Another advantage is the fact that there is no snap movement in moving a shield into a locked position over a contaminated needle causing the flinging or splattering of blood from the contaminated needle. Also, as will be understood from the discussion above, every holder is a potential safety holder when the need arises.

While the cooperating locking means on each end of the holder of the invention has been described as a bayonet-type arrangement, it will be understood that other cooperating locking means may be arranged such as a friction fit lock or a screw thread connection. However, it is preferred to use a locking means which is best described as a cooperating bayonet-type arrangement.

Other objects and advantages of this invention will be apparent from the following description, the accompanying drawings and the appended claims.

DESCRIPTION OF THE DRAWINGS

FIG. 4a is a longitudinal side view partially in phantom showing the positioning of two holders of the invention immediately prior to the one holder being locked together with the second holder so as to cover a contaminated needle;

FIG. 4b shows the same two holders as in FIG. 4a with the two holders of the invention locked together;

DETAILED DESCRIPTION OF THE INVENTION

Figure 1:
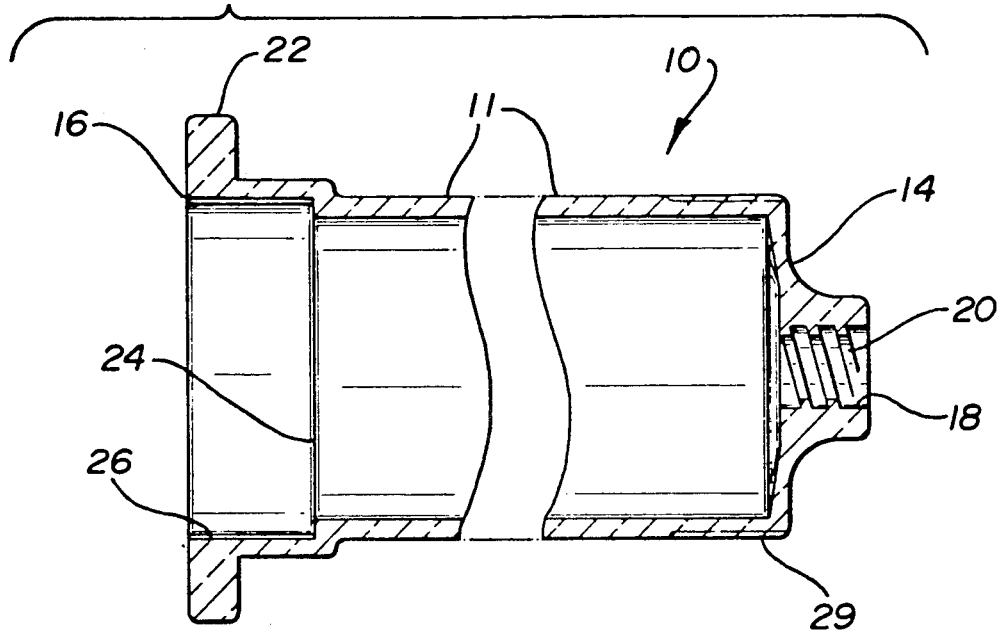
FIG. 1 is a longitudinal sectional view illustrating the device of the invention in the form of a blood draw holder.

Referring to the drawings in which like reference characters refer to like parts throughout the several views thereof, FIG. 1 shows a longitudinal sectional and expanded view of a standard conventional blood draw holder, modified in accordance with the invention. That is, holder 10 has the usual barrel shaped or cylindrical side wall 11 with a closed end 14 and an open end 16. Adjacent the open end 16 is a stepped portion 24 which provides for insertion of the closed end of another modified blood draw holder 10 of the invention. The open end 16 includes spaced openings 26 which cooperate with tabs 29 placed on the outer surface of barrel 11 adjacent the closed end 14 of the modified holder of the invention. As shown in FIG. 1, the closed end 14 of holder 10 includes the conventional bore 18 with screw threads 20 for receiving the hub of a double ended needle utilized to take a blood sample.

Figure 2:
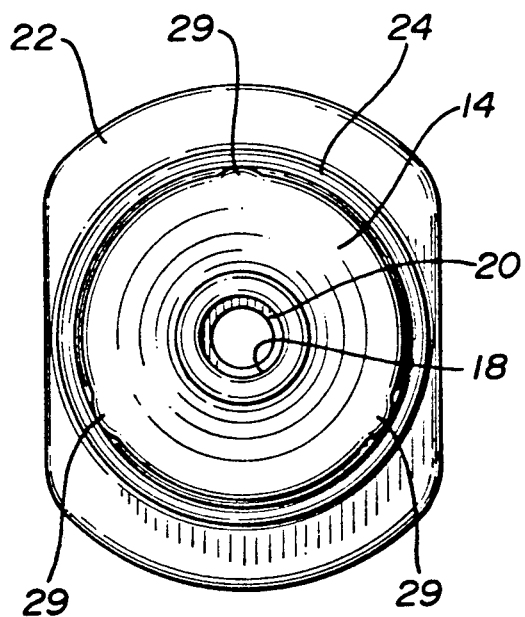
FIG. 2 is an end view of the device of FIG. 1 as viewed from the right-hand end thereof.
Figure 3:
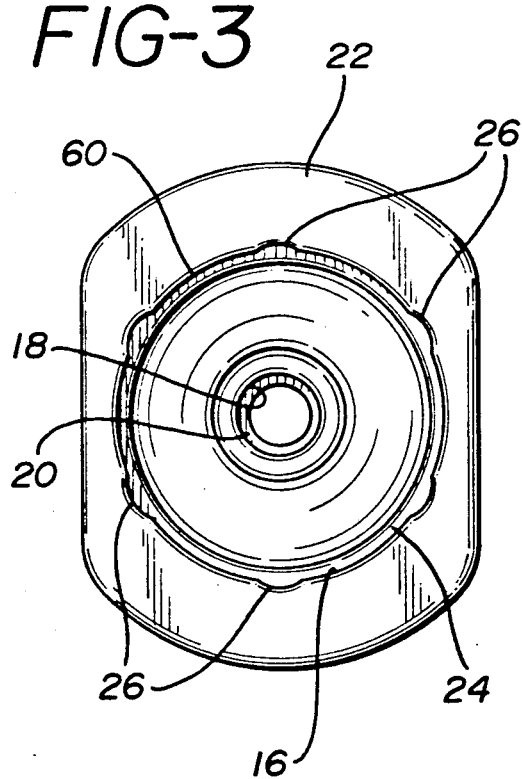
FIG. 3 is an end view of the device of FIG. 1 as viewed from the left hand end of the device shown in FIG. 1.

Referring now to FIG. 2, as shown, the modified arrangement includes three equally spaced tabs 29 positioned around the circumference of the barrel wall 11 of the modified holder of the invention. The tabs 29 cooperate with indentations 26, as shown in FIG. 3, (which may number 6) positioned circumferentially around the open end 16 of the modified blood draw holder 11 of the invention. Also shown in FIG. 3 is the conventional flange 22 which helps the user hold the blood draw holder 10 between two fingers during insertion and taking of a blood sample.

FIGS. 4a and 4b illustrate generally the positioning of two of the modified holders of the invention immediately prior to insertion of the contaminated needle 41 into the unused holder 10a shown in phantom in FIGS. 4a and 4b. That is, a needle hub 38 carries a double ended needle 40, 42. As will be understood by practitioners in the-art, needle end 42 has a rubber sleeve, not shown, covering it so that once an evacuated tube has been removed from needle 42, the rubber sleeve covers the needle end 42 to prevent the loss of blood while the needle point 41 is still inserted into the vein of a patient.

Thereafter, a second evacuated tube may be inserted into the blood draw holder 10 until the necessary number of evacuated tubes are filled with collected blood of the patient. Thereafter, the needle 41 is removed from the vein of a patient and it is contaminated with the blood of the patient. In accordance with this invention, the user then positions the unused holder 10a, as discussed above, and shown in phantom over the contaminated end 41 of the needle 40.

Thereafter, the two holders 10a and 10 are locked together as illustrated by the arrow 17 in a twisting action. This causes the needle 41 to be entirely covered by the unused holder 10a, and the locked assembly is discarded.

Figure 7:
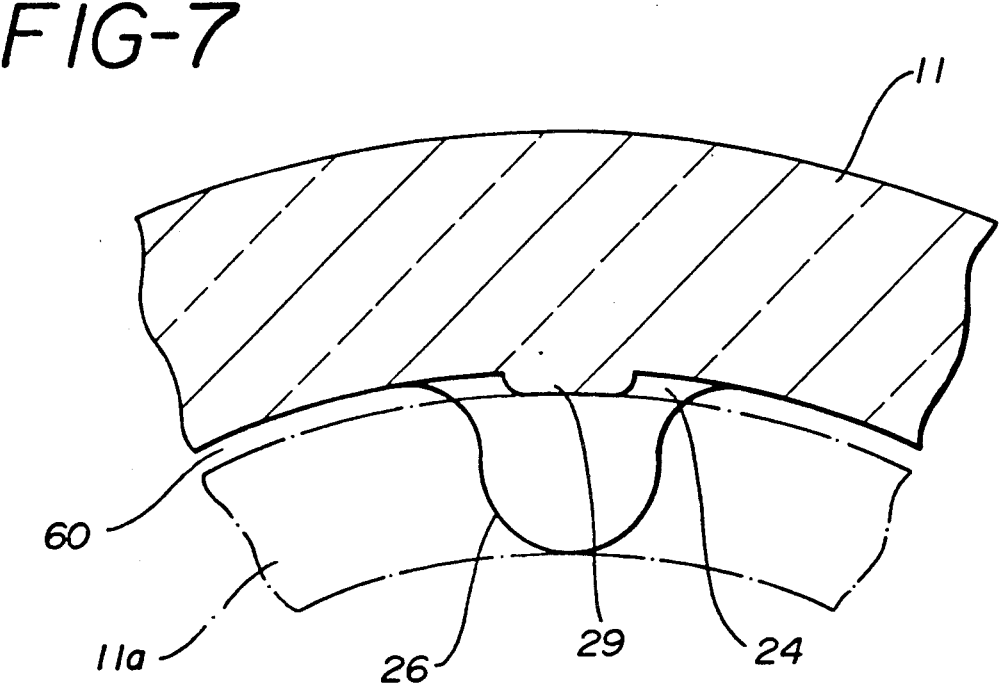
FIG. 7 is an enlarged view in section of a portion of the interlocking arrangement between two of the modified holders of the invention and illustrating the locking arrangement.

As further illustrative of the invention, reference is made to FIG. 7 which shows an enlarged sectional view of a locking tab 29 and opening 26. Thus, when a used holder 11 carrying a double ended needle as shown in FIG. 4a is inserted into an unused holder 11a, the locking tabs 29 and openings 26 may be positioned adjacent each other to provide the final insertion and then they are twisted as illustrated by the arrow 17 in FIG. 4b so that the tab 29 slides under the edge 60 as shown in FIG. 7 of the unused holder 11a. This has the effect of locking the two holders together so that the needle is completely covered by the unused holder 11a. The twisting action may, as discussed above, be a cooperating screw thread type connection instead of the connection described.

Figure 5:
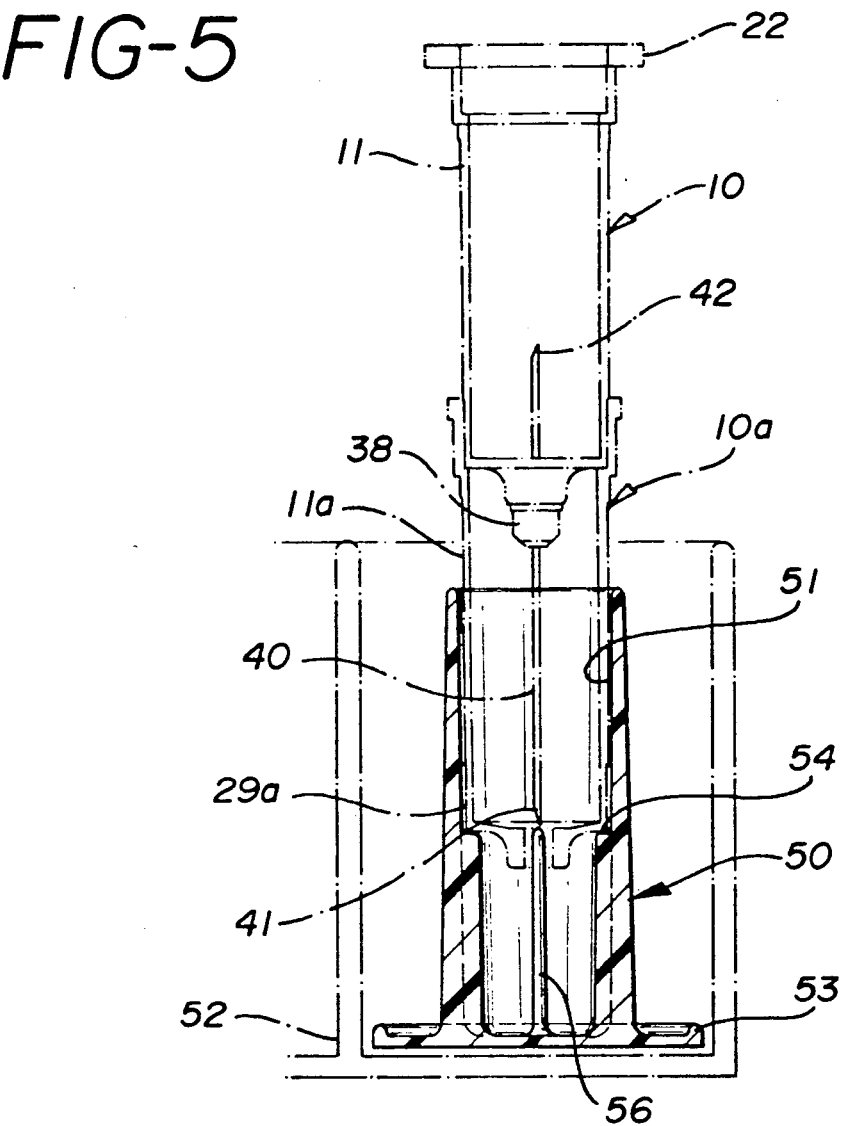
FIG. 5 is a view in elevation and partly in phantom illustrating the positioning of the modified holders of the invention and illustrating the locking socket portion of the invention and how the user positions the various parts in order to protect against needle stick.

As a further feature of this invention, reference is made to FIG. 5 which shows one embodiment of the locking socket arrangement 50 of the invention. That is, the socket 50 may be placed or inserted into a container 52 on a phlebotomist s tray or cart and reused many times. The base 53 thereof will have, for example, a double-sided tape on the bottom surface thereof to adhere the socket 50 to container 52. For this reason, the socket 50 is a semi permanent structure placed there for receiving, sequentially, unused modified holders 10a of the invention. That is, positioned in socket 50 is the structure as illustrated in FIGS. 4a and 4b. Socket 50 includes a cooperating locking arrangement 54 in bore 51, including tabs 56 for engaging tabs 29a on holder 10a to prevent rotation thereof during locking of a used holder 10 therein.

Thus, the unused holder 10a is locked in place in socket 50 for receiving the used holder 10 and its contaminated needle 40 and point 41 as illustrated in FIG. 5 in phantom. The user merely inserts the used holder 10 into the unused holder 10a fixed in socket 50 and twists to join the two holders 10a and 10 together. Thereafter, the two may be removed from socket 50 and discarded together so as to maintain the contaminated point 41 of needle 40 completely covered.

Figure 6:
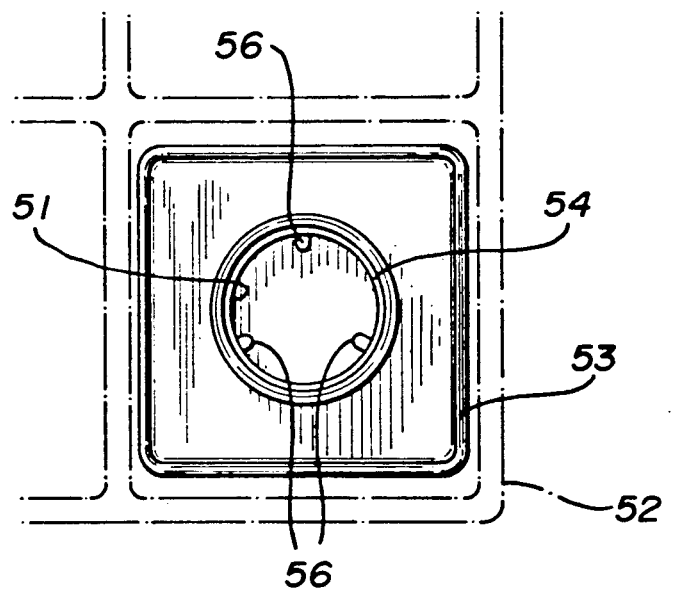
FIG. 6 is a top plan view of the arrangement shown in FIG. 5.

FIG. 6 is a top plan view of the device of FIG. 5 with the holders not inserted. As shown in FIG. 6, the socket arrangement has locking tabs 56 similar to the locking tabs 29 of an unused holder as shown in FIG. 2. It will be understood that it is desirable and appropriate, in accordance with this invention, to use such a fixed socket arrangement such as 50 illustrated in FIG. 5. However, the user need not, if in a place where a socket 50 is not available, use such a device. In such an incident, the user may simply grab an unused holder, lay it on a table or other surface, and insert the contaminated needle into the large open end of the unused holder and lock the two holders together as more fully described below in describing FIGS. 14 and 15. However, utilizing the socket arrangement 50 of the invention allows the user to use only one hand for finally fixing the contaminated needle point into the unused holder fixed in the socket 50.

Figure 8:
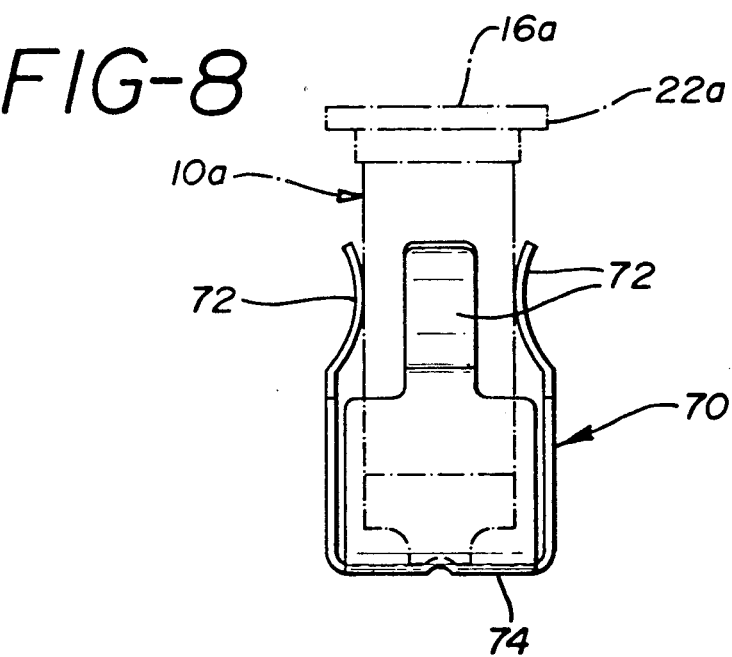
FIG. 8 illustrates a further arrangement of socket for positioning on a phlebotomist's tray for providing the holding of the two modified holders of the invention during the interlocking procedure thereof.
Figure 9:
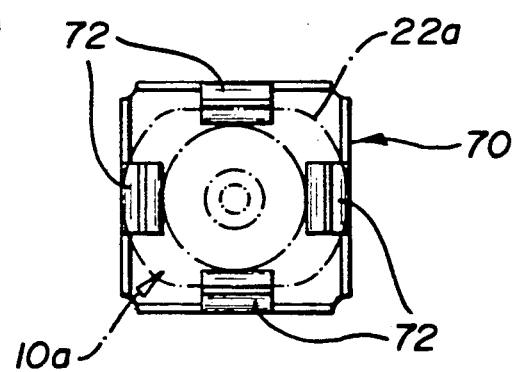
FIG. 9 is a top plan view of the device of FIG. 8.

FIGS. 8 and 9 illustrate a further socket arrangement 70 which may be fixed to a phlebotomist's tray. That is, the socket arrangement 70 has a flat bottom surface 74 which may incorporate a double-sided tape, not shown, for adherence to the phlebotomist's tray or cart. The socket 70 includes four diametrically placed spring mounted fingers 72 for receiving an unused holder 10a in place. The spring like fingers 72, comprised of a flexible material, serve to hold the unused holder 10a in place when the contaminated needle of a used holder is inserted into the open end 16a of the unused holder 10a as shown in FIG. 8. FIG. 9 is a top plan view of the device shown in FIG. 8 and illustrates the positioning of the upwardly extending flexible fingers 72 for gripping the unused holder 10a.

Figure 10:
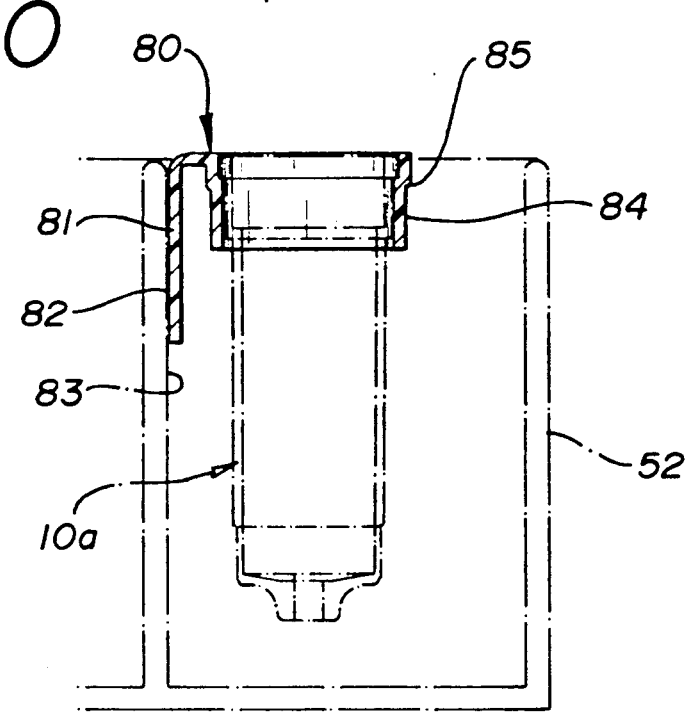
FIG. 10 is a side view in elevation and partly in phantom showing a further socket locking arrangement for positioning on a phlebotomist's tray in the form of a socket which may be adhered to the side wall of a tray container.

FIG. 10 illustrates a further socket arrangement 80 for fixing at a phlebotomist's station this case, the arrangement 80 has a circular receiving ring 84 for receiving an unused holder 10a. The ring 84 has a stepped arrangement 85 for preventing the holder 10a from falling through ring 84. Attached to the ring 84 is a depending flange 81 which may have on the outside surface 82 thereof a double sided tape, not shown, for adhering to the wall 83 of a container 52 of some sort shown in phantom in FIG. 10. The ring 84 may be of a dimension which will cause frictional gripping of a holder 10a suspended as shown therein.

Figure 11:
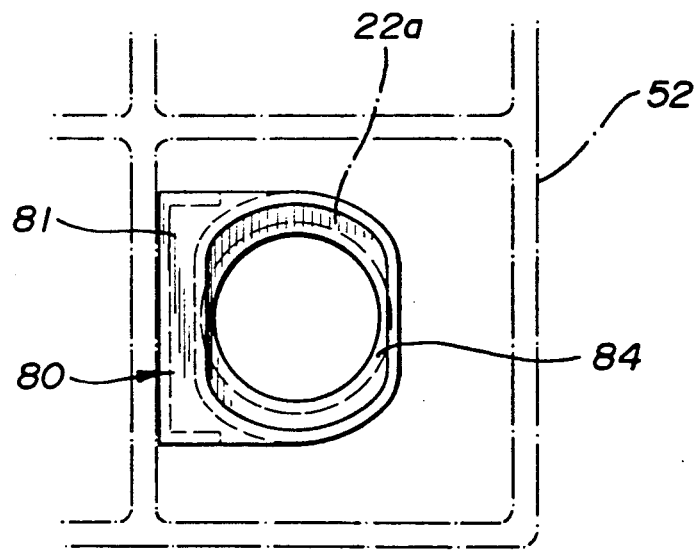
FIG. 11 is a top plan view of the device of FIG. 10.

FIG. 11 is a top plan view of the arrangement of FIG. 10 illustrating the top surface of the ring 84 as it relates to the overhanging flange 81.

Figure 12:
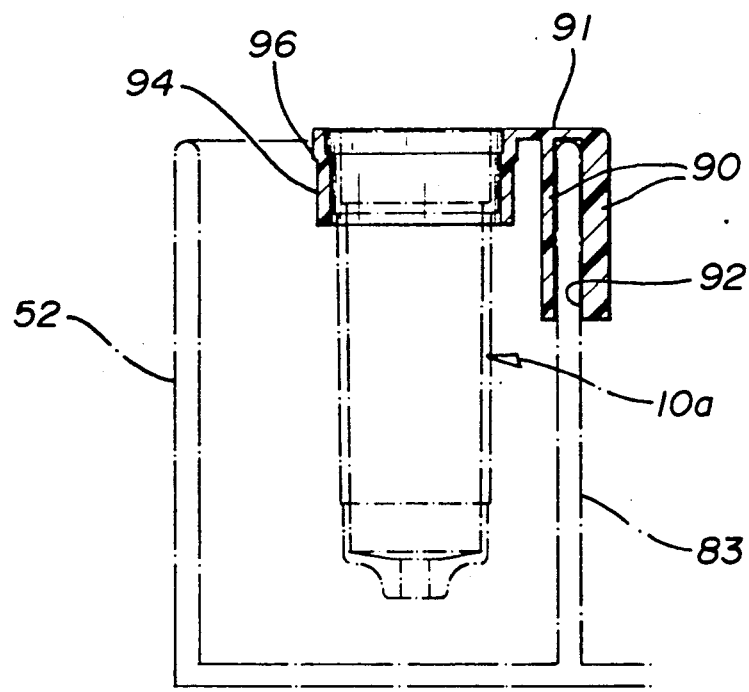
FIG. 12 is an illustration of a further locking socket arrangement which may be utilized on a phlebotomist's tray in the form of a hanging type socket which may be affixed over the wall of a container on a phlebotomist's tray.
Figure 13:
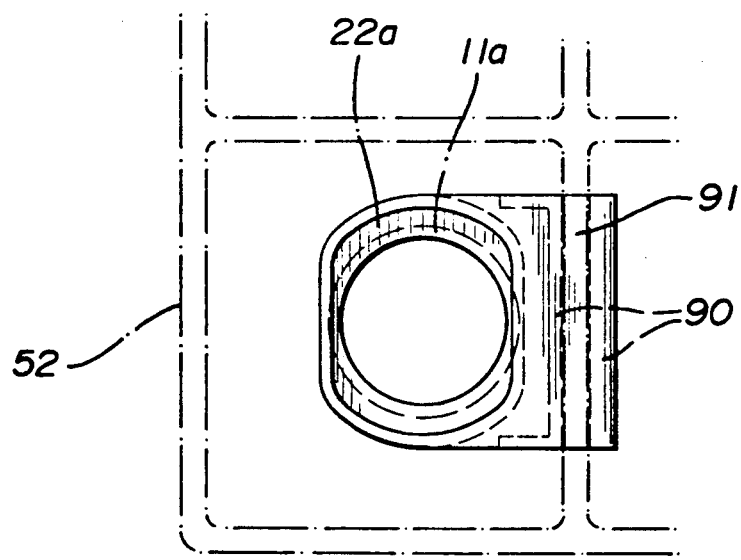
FIG. 13 is a top plan view of the device of FIG. 12.

FIG. 12 illustrates a further hanging ring arrangement for mounting on the wall 83 of a container 52 positioned at a phlebotomist's tray or station. In this case, the ring 94 has a top plate 91 with depending spaced flanges 90 defining a space 92 for receiving the upper edge of a wall 83 of a container 52. Thus, the ring 94 is positioned on a semi permanent basis for receiving a plurality of unused modified holders 10a of the invention for in turn receiving a used modified holder of the invention with its contaminated needle. The abutment 96, is utilized to help position and hold the unused holder 10a until it is locked in place with the used holder which is inserted therein.

Figure 14:
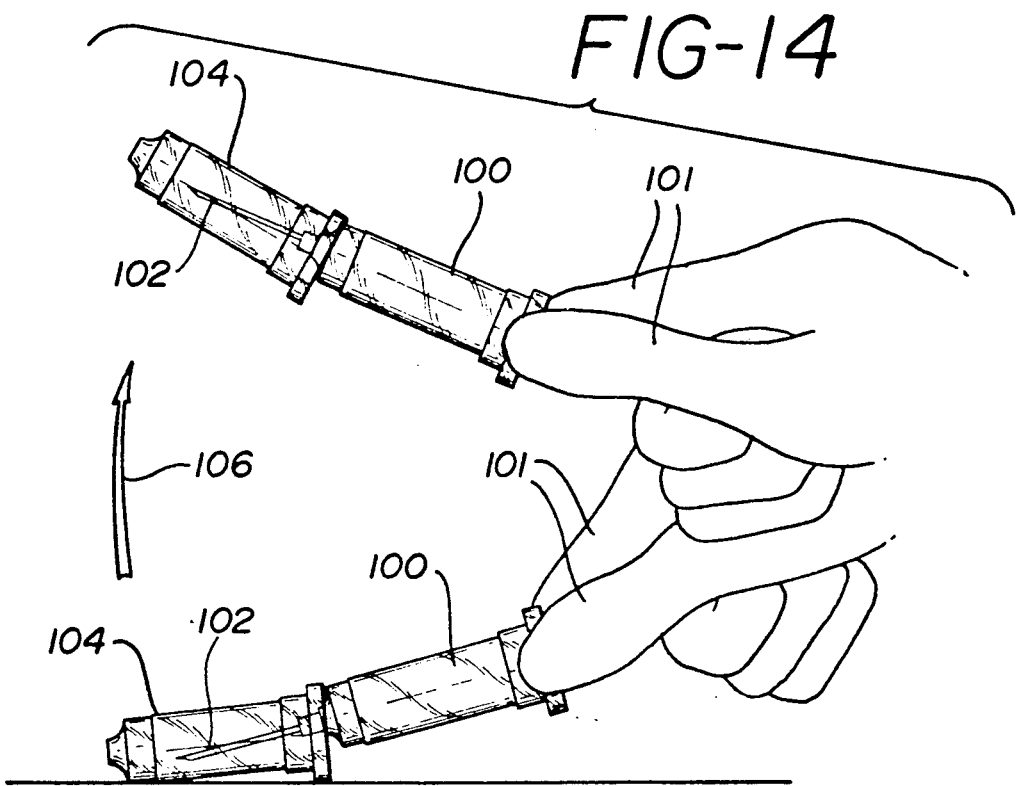
FIGS. 14 and 15 are a diagrammatic indication of one procedure for interlocking two holders of the invention together to cover a contaminated needle without the use of the separate socket locking arrangement.
Figure 15:
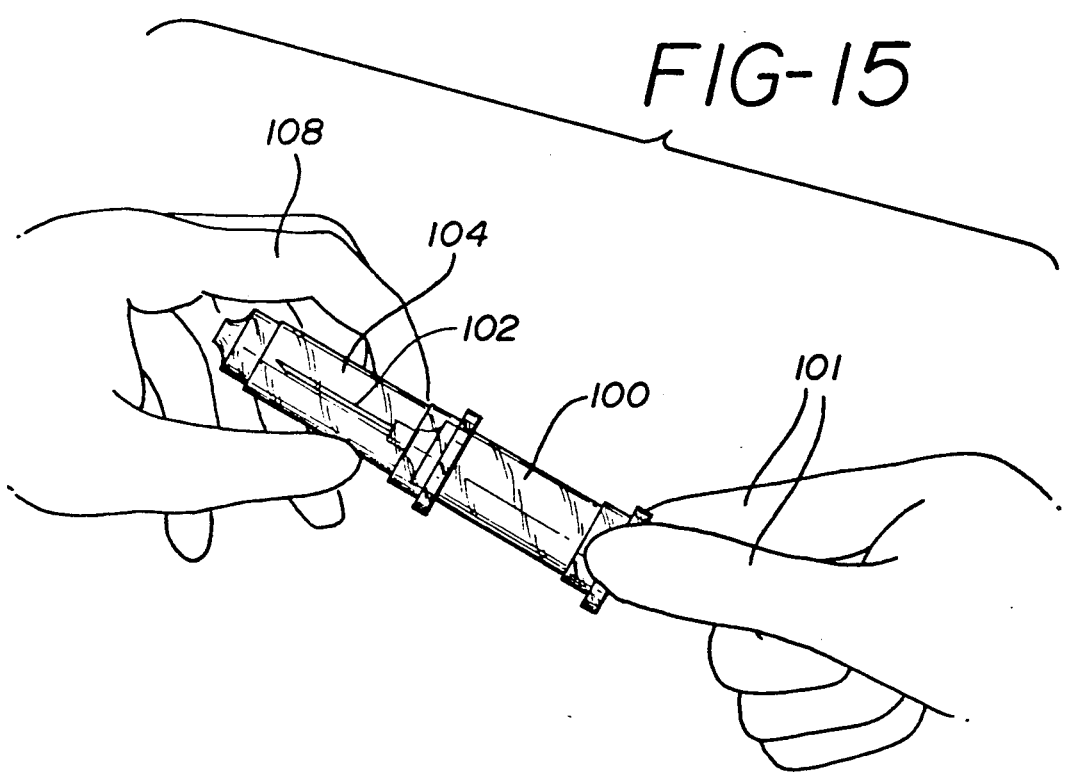

FIGS. 14 and 15 illustrate a procedure for covering a contaminated needle using two holders of the invention wherein the separate socket is not readily available. Thus, referring to FIG. 14, a holder 104 of the invention is placed on a horizontal surface 103. Thereafter, the user may grasp the holder 100 containing a contaminated needle 102 may be grasped by the fingers 101 of the user as illustrated and insert contaminated needle 102 into the open end of unused holder 104. Subsequent to this movement, the two holders 100, 104 are moved in the direction of arrow 106 so that the user may utilize the other hand 108 to grasp holder 104, and twist holders 100, 104 together into locked position as described above.

Thus, as will be appreciated from the above, there is provided in accordance with this invention, a conventional needle holder modified in a simple fashion to provide cooperating locking means at each end thereof so that the holder may be itself used as a cover for a contaminated needle in another holder modified in the same fashion having a double ended needle inserted therein for taking a blood sample.

Because of the arrangement herein, all of the holders may be manufactured from a single mold which reduces the cost substantially of the structure of the invention. No cumbersome extra cooperating locking arrangements are required for moving a coaxial shield from a non permanent semi-locking position coaxial with the holder to a final position locked in place over a contaminated needle. In addition, the phlebotomist is relieved from this kind of cumbersome and bulky holder arrangement during the sensitive time when a needle is being inserted into the vein of a patient and blood withdrawn therefrom.

This, in turn, eliminates the need to stock plain blood draw holders, or special safety holders. Only the holder of the invention is required, thus reducing hospital inventory costs. Also, no special decision has to be made in a selection of holders prior to the blood draw procedure. Only the holder of the invention is required, regardless of the circumstances.

The locking socket of the invention, in turn, provides a relatively easy way of locking the contaminated used holder and the non contaminated unused holder together with a single hand rather than having to use both hands. It is positioned adjacent to the phlebotomist's activities at all times so that it may be utilized for each blood draw session.

The assembly of the invention, as will be understood, can be mass produced from a variety of materials including, for example, polyethylene and polypropylene. Materials will be selected which will provide a degree of resiliency for the purpose of providing cooperative movement relative to the cooperating locking means of the assembly of the invention.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas one form of cooperating locking arrangement is shown and described as a simple bayonet connection, cooperating screw threads will provide the same simple locking of the two parts together. In addition, frictional gripping surfaces may be used.

What is claimed is:

1. A blood draw needle holder for use in taking blood samples, comprising
   (a) an elongated tubular body;
   (b) said body having an open end and a substantially closed end;
   (c) a flange handle extending circumferentially around said open end;
   (d) a bore positioned in said closed end, said bore being coaxial with said elongated tubular body;
   (e) said bore having screw threads therein for receiving the hub of a double-ended blood draw needle;
   (f) first cooperating locking means positioned on the outer circumferential surface of said elongated tubular body adjacent said closed end;
   (g) said first cooperating locking means including
      (1) a recessed surface;
      (2) a plurality of tabs extending from said recessed surface;
      (3) said tabs being spaced circumferentially around said tubular body;
   (h) second cooperating locking means positioned on the internal surface of said elongated tubular body adjacent said open end; and
   (i) said second cooperating locking means including
      (1) said tubular body having an area of enlarged diameter adjacent said open end, said enlarged diameter area stepped from the remaining surface of said tubular body;
      (2) said area of enlarged diameter having a plurality of circumferentially spaced indentations for receiving the tabs of said first cooperating locking means on another identical blood draw holder;
   (j) whereby the said open end of said blood draw needle holder may be locked with the closed end of an identical blood draw needle holder or visa versa.

2. The blood draw holder of claim 1, further comprising
   (a) said first and second cooperating locking means being integral with said elongated tubular body.

3. The blood draw holder of claim 1, further comprising
   (a) said first and second cooperating locking means being cooperating helical screw threads.

4. An assembly for preventing accidental body fluid contaminated needle sticks, comprising
   (a) two blood draw needle holders;
   (b) each of said blood draw needle holders including
      (1) an elongated tubular body;
      (2) said body having an open end and a substantially closed end;
      (3) a flange handle extending circumferentially around said open end;
      (4) a bore positioned in said closed end, said bore being coaxial with said elongated tubular body;
      (5) said bore having screw threads therein for receiving the hub of a double-ended blood draw needle;
      (6) first cooperating locking means positioned on the outer circumferential surface of said elongated tubular body adjacent said closed end; and
      (7) second cooperating locking means positioned on the internal surface of said elongated tubular body adjacent said open end;
      (8) whereby the said open end of said blood draw needle holder may be locked with the closed end of an identical blood draw needle holder or visa versa;
   (c) said first cooperating locking means including
      (1) a recessed surface;
      (2) a plurality of tabs extending from said recessed surface;
      (3) said tabs being spaced circumferentially around said tubular body;
   (d) said second cooperating locking means including
      (1) said tubular body having an area of enlarged diameter adjacent said open end, said enlarged diameter area stepped from the remaining surface of said tubular body;
      (2) said area of enlarged diameter having a plurality of circumferentially spaced indentations for receiving the tabs of said first cooperating locking means on another identical blood draw holder;
   (e) a double-ended blood draw needle;
   (f) said needle having a hub with screw threads;
   (g) said hub positioned in the bore of said closed end of one of said blood draw needle holders; and
   (h) whereby when said blood draw needle becomes contaminated, the closed end of its associated blood draw needle holder may be inserted into the open end of the other needle holder for locking the said first cooperating locking means of said needle held holder with the said second cooperating locking means of said needleless holder.

5. The assembly of claim 4, further comprising
   (a) said first and second cooperating locking means being integral with said elongated tubular body.

6. The assembly of claim 4, further comprising
   (a) said first and second cooperating locking means being cooperating helical screw threads.

* * * * *